(12) United States Patent
Ohmae et al.

(10) Patent No.: US 10,099,866 B2
(45) Date of Patent: Oct. 16, 2018

(54) TRANSPORT APPARATUS AND TRANSPORT METHOD

(71) Applicant: SYSMEX CORPORATION, Kobe-shi, Hyogo (JP)

(72) Inventors: Yuichiro Ohmae, Kobe (JP); Hiroo Tatsutani, Kobe (JP); Nobuyoshi Yamakawa, Kobe (JP)

(73) Assignee: SYSMEX CORPORATION, Kobe-shi (JP)

( * ) Notice: Subject to any disclaimer, the term of this patent is extended or adjusted under 35 U.S.C. 154(b) by 23 days.

(21) Appl. No.: 14/838,534

(22) Filed: Aug. 28, 2015

(65) Prior Publication Data

US 2016/0060046 A1    Mar. 3, 2016

(30) Foreign Application Priority Data

Aug. 29, 2014  (JP) ................................. 2014-175906

(51) Int. Cl.
| | |
|---|---|
| *B65G 47/34* | (2006.01) |
| *B65G 47/88* | (2006.01) |
| *G01N 35/04* | (2006.01) |

(52) U.S. Cl.
CPC ............. *B65G 47/34* (2013.01); *B65G 47/88* (2013.01); *G01N 35/04* (2013.01)

(58) Field of Classification Search
CPC ......... G01N 35/04; B65G 47/34; B65G 47/88
See application file for complete search history.

(56) References Cited

U.S. PATENT DOCUMENTS

| | | | |
|---|---|---|---|
| 5,346,352 A * | 9/1994 | Ito ........................ | B23Q 7/1442 198/718 |
| 6,117,683 A | 9/2000 | Kodama et al. | |
| 2006/0216199 A1* | 9/2006 | Koike .................. | G01N 35/026 422/65 |
| 2010/0159603 A1* | 6/2010 | Hamada ................. | G01N 35/00 436/47 |
| 2010/0166606 A1* | 7/2010 | Koike .................... | G01N 35/04 422/65 |

(Continued)

FOREIGN PATENT DOCUMENTS

| | | |
|---|---|---|
| EP | 2299282 A2 | 3/2011 |
| JP | H6-82565 U | 11/1994 |

(Continued)

*Primary Examiner* — Benjamin R Whatley
(74) *Attorney, Agent, or Firm* — Metrolexis Law Group, PLLC (57) ABSTRACT

A transport apparatus transports sample holder racks. The apparatus employs a first transport unit that moves the rack in a path between two ends of the transport apparatus, a rack sender unit that extends in a first direction that intersects the path, a second transport unit dimensioned parallel to the first transport unit and with the rack sender unit interposed therebetween, which locates the sample container held in the rack at a sample loading position of a measurement device, and a first movable member capable of moving in the first direction between the first and the second transport units. The apparatus has movable portions that alternately stop the rack movement, and push the rack such that optimal movement is achieved whereby the rack moves beyond the rack sender unit to the second transport unit as the first movable member moves in the first direction.

11 Claims, 4 Drawing Sheets

(56) References Cited

U.S. PATENT DOCUMENTS

2011/0160899 A1* 6/2011 Tatsutani ............ G01N 35/0092
700/218
2011/0243792 A1* 10/2011 Tatsutani ............ G01N 35/0092
422/65
2011/0256022 A1* 10/2011 Akutsu ............ G01N 35/00603
422/65

FOREIGN PATENT DOCUMENTS

| JP | 2001-074754 A | | 3/2001 |
|----|---------------|---|--------|
| JP | 2001074754 A | * | 3/2001 |
| JP | 2002-311035 A | | 10/2002 |
| JP | 2010-91417 A | | 4/2010 |
| JP | 2011-137749 A | | 7/2011 |

* cited by examiner

TRANSPORT APPARATUS AND TRANSPORT METHOD

CROSS REFERENCE TO RELATED APPLICATIONS

This application claims priority to prior Japanese Patent Application No. 2014-175906 filed on Aug. 29, 2014 entitled "TRANSPORT APPARATUS," the entire contents of which are hereby incorporated by reference.

BACKGROUND

This disclosure relates to a transport apparatus that transports a rack holding a sample container.

There is a transport apparatus that transports a rack holding a sample container (for example, Japanese Patent Application Publication No. 2011-137749 (Patent Literature 1)).

Patent Literature 1 discloses a transport apparatus that transports a sample to a measurement device. The transport apparatus includes a first transport unit, a second transport unit, a rack sender unit, a movable member, and a rack transfer member. The first transport unit transports a rack in longitudinal directions of the first transport unit between both ends of the transport apparatus. The rack sender unit extends a first direction orthogonal to the first transport unit. The rack sender unit is located between the first transport unit and the second transport unit. The second transport unit locates a sample container held in a rack at a sample loading position of a measurement device. The movable member is movable in the first direction between the first transport unit and the rack sender unit. The rack transfer member is a pair of hook members. The rack transfer member is arranged at the rack sender unit. In order to move a rack on the first transport unit to the rack sender unit, the movable member stops the rack on the first transport unit once, and then moves the stopped rack toward the rack sender unit. At the rack sender unit, the rack is passed from the movable member to the rack transfer member. The rack thus passed to the rack transfer member is moved to the second transport unit by the rack transfer member.

SUMMARY

An embodiment of a transport apparatus that transports a rack that holds a sample container, comprising: a first transport unit that transports the rack in a longitudinal direction between two ends of the transport apparatus; a rack sender unit that extends in a first direction that intersects a longitudinal direction of the first transport unit; a second transport unit that extends parallel to the first transport unit with the rack sender unit interposed therebetween and locates the sample container held in the rack at a sample loading position of a measurement device; and a first movable member capable of moving in the first direction between the first transport unit and the second transport unit, wherein the first movable member comprises a first portion that stops, at a rack stop position, the rack transported by the first transport unit, and a second portion that pushes, in the first direction, a side surface of the rack located at the rack stop position, and wherein the second portion moves the rack at the rack stop position beyond the rack sender unit to the second transport unit as the first movable member moves in the first direction.

DETAILED DESCRIPTION

Embodiments are explained with reference to drawings. In the respective drawings, the same constituents are designated by the same reference numerals and duplicate explanation concerning the same constituents is basically omitted. Drawings are provided to illustrate representative examples only. No dimensional proportions in the drawings shall impose a restriction on the embodiments. For this reason, specific dimensions and the like should be interpreted with the following description taken into consideration. In addition, the drawings include parts whose dimensional relationship and ratios differ from one drawing to another.

With reference to FIGS. 1 to 4, a configuration of transport apparatus 10 according to an embodiment is described.

Figure 1:
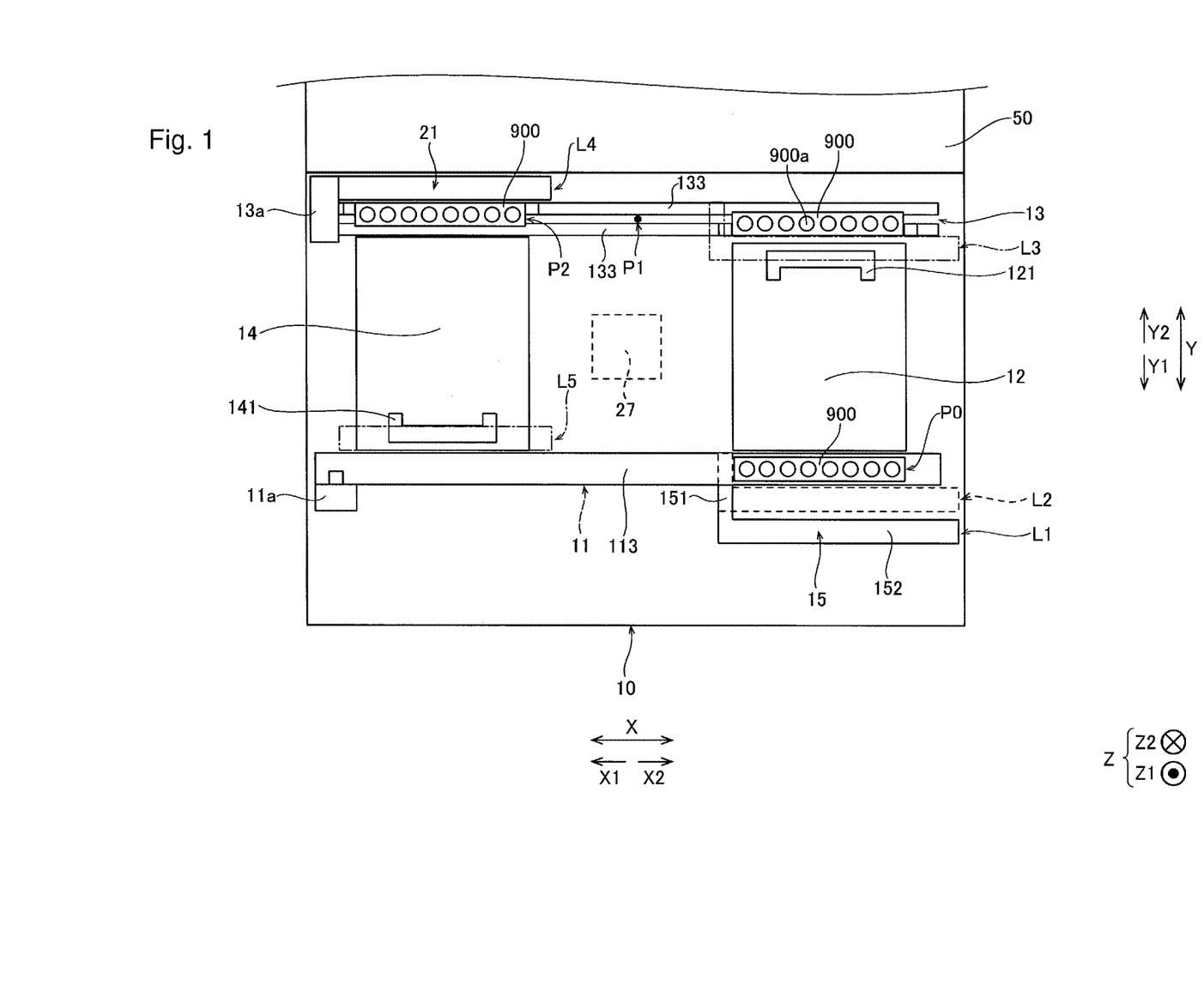
FIG. 1 is a schematic diagram illustrating a transport apparatus according to an embodiment.

Transport apparatus 10 illustrated in FIG. 1 transports rack 900 holding sample containers 900a, to sample loading position P1 at which measurement device 50 loads a sample. In a preferred embodiment, measurement device 50 is a urine testing device that sucks a urine sample in each sample container 900a and tests the urine.

Transport apparatus 10 includes first transport unit 11, rack sender unit 12, second transport unit 13, and rack delivery unit 14.

First transport unit 11 includes transport belt 113 that transports rack 900 in longitudinal directions (X1 and X2 directions). Transport belt 113 has along side extending along an X axis. Transport belt 113 transports rack 900 along the X axis between both ends (X2-side end and X1-side end) of first transport unit 11.

Note that, in this specification, an axis orthogonal to first transport unit 11 is called a Y axis; an X1 direction is called a transport direction; and a vertically downward direction in the state of installation of transport apparatus 10 is called a downward direction (Z2 direction).

Stopping member 11a is arranged near the X1-side end of first transport unit 11. Stopping member 11a is capable of moving between a position interfering with first transport unit 11 and a position not interfering with first transport unit 11. When another transport apparatus is connected to a downstream part in the transport direction of transport apparatus 10, stopping member 11a controls the timing to feed rack 900 to the downstream transport apparatus.

Rack sender unit 12 extends in a Y2 direction. Rack sender unit 12 is sandwiched, at its both sides on the Y axis, by second transport unit 13 and first transport unit 11.

Rack sender unit 12 preferably includes restriction unit 121. Restriction unit 121 is arranged near the Y2-side end of rack sender unit 12. Restriction unit 121 projects above the upper surface of rack sender unit 12 by the driving of a motor not illustrated. When projecting above the upper surface of rack sender unit 12, restriction unit 121 comes into contact with rack 900 moving in rack sender unit 12. By switching the modes of restriction unit 121 between a projected mode and a non-projected mode, restriction unit 121 is capable of positional change between a contact mode where restriction unit 121 is to come into contact with rack 900 and a non-contact mode where restriction unit 121 is kept out of contact with rack 900. Restriction unit 121 restricts, in the contact mode, the movement of rack 900 from rack sender unit 12 to second transport unit 13. Restriction unit 121 thereby allows rack 900, which holds samples yet to be sucked by measurement device 50 at sample loading position P1, to remain in rack sender unit 12.

Second transport unit 13 is arranged at the Y2 side of first transport unit 11 with rack sender unit 12 interposed therebetween. Second transport unit 13 is arranged to extend parallel with first transport unit 11 (X1 direction) with rack sender unit 12 interposed therebetween. Second transport unit 13 is arranged at a position closer to measurement device 50 than first transport unit 11.

Second transport unit 13 includes two transport belts 133. Second transport unit 13 is capable of transporting rack 900 in the X1 direction.

Second transport unit 13 is capable of positioning each sample container 900a held in rack 900 at sample loading position P1 where measurement device 50 loads a sample. Second transport unit 13 transports rack 900 transported from rack sender unit 12 toward rack delivery unit 14 via sample loading position P1. Second transport unit 13 is capable of arranging two racks 900 at different positions on the X axis and transporting them individually.

Stopping member 13a that stops rack 900 at rack stop position P2 is arranged outside second transport unit 13 on its X1 side.

Rack delivery unit 14 is arranged between first transport unit 11 and second transport unit 13. Rack delivery unit 14 extends in the Y2 direction intersecting the extending direction of first transport unit 11. Rack 900 having passed through sample loading position P1 is sent out to rack delivery unit 14.

Rack delivery unit 14 includes restriction unit 141. Restriction unit 141 is arranged near the Y1-side end of rack delivery unit 14. Restriction unit 141 projects above the upper surface of rack delivery unit 14 by the driving of a motor (not shown). By switching the modes of restriction unit 141 between a projected mode and a non-projected mode, restriction unit 141 can be changed between a contact mode of contacting rack 900 moving in rack delivery unit 14 and a non-contact mode of not contacting rack 900, similarly to restriction unit 121 of rack sender unit 12. Restriction unit 141 thus restricts, in the contact mode, the movement of rack 900 from rack delivery unit 14 to first transport unit 11. Restriction unit 141 thereby allows rack 900, which holds samples aspirated at sample loading position P1 already, to remain in rack delivery unit 14.

Note that restriction unit 141 may be used in a state of projecting above the upper surface of rack delivery unit 14 at all times. Rack 900 configured to remain in rack delivery unit 14 in this case can be drawn to the outside of transport unit 10 by a user.

Transport apparatus 10 further includes first movable member 15 provided for rack sender unit 12 and second movable member 21 provided for rack delivery unit 14. First movable member 15 includes first portion 151 and second portion 152. First portion 151 is formed at the X1-side end of second portion 152. First portion 151 projects from second portion 152 to the Y2 side. First portion 151 allows rack 900 being transported by first transport unit 11 to stop at rack stop position P0. Second portion 152 extends in the longitudinal directions of rack 900 on first transport unit 11. In other words, second portion 152 has a long side extending along the X axis.

First movable member 15 is movable along the Y axis. More specifically, first movable member 15 is movable between first position L1 being the end point in the Y1 direction and second position L3 being the endpoint in the Y2 direction. First movable member 15 may be located at stop position L2 between first position L1 and second position L3.

First position L1 is a position of first movable member 15 where neither first portion 151 nor second portion 152 protrudes on first transport unit 11, and is the position of origin of first movable member 15. When first movable member 15 is located at first position L1, first portion 151 does not interfere with rack 900 being transported by first transport unit 11. In the state where first movable member 15 is located at first position L1, first transport unit 11 can move rack 900 beyond the position of first movable member 15 to its X1-side end.

Stop position L2 is a position where first portion 151 protrudes on first transport unit 11 but second portion 152 does not protrude on first transport unit 11. In the state where first movable member 15 is located at stop position L2, rack 900 being transported on first transport unit 11 is stopped at rack stop position PO by first portion 151.

Second position L3 is a position where first portion 151 protrudes on second transport unit 13 and second portion 152 abuts on second transport unit 13. As first movable member 15 moves in the Y2 direction from stop position L2 to second position L3, first movable member 15 can push rack 900 at rack stop position PO using second portion 152 and move the rack beyond rack sender unit 12 to second transport unit 13.

In a plan view, second movable member 21 is substantially in the form of a rectangle having a long side on the X axis. Second movable member 21 has the same configuration as first movable member 15 except that second movable member 21 includes no portion equivalent to first portion 151. Second movable member 21 is movable between position L4 where second movable member 21 is not placed on second transport unit 13 and position L5 where second movable member 21 pushes and places rack 900 on rack delivery unit 14. Position L4 is the position of origin of second movable member 21. Position L5 is a position where second movable member 21 abuts on first transport unit 11, and is a foremost position in the movable range of second movable member 21.

Second movable member 21 can move rack 900 located on second transport unit 13 to a Y1-side end portion of rack delivery unit 14. This allows rack 900, which holds sample containers 900a subjected to a sample loading operation at sample loading position P1, to remain in rack delivery unit 14.

Controller 27 includes a central processing unit (CPU) and a storage unit. Controller 27 performs control related to a transport operation of transport apparatus 10, based on a program stored in the storage unit. How controller 27 controls the units is to be described later.

Next, mechanisms to drive first movable member 15 and second movable member 21 are described with reference to FIGS. 2 and 3.

Figure 2:
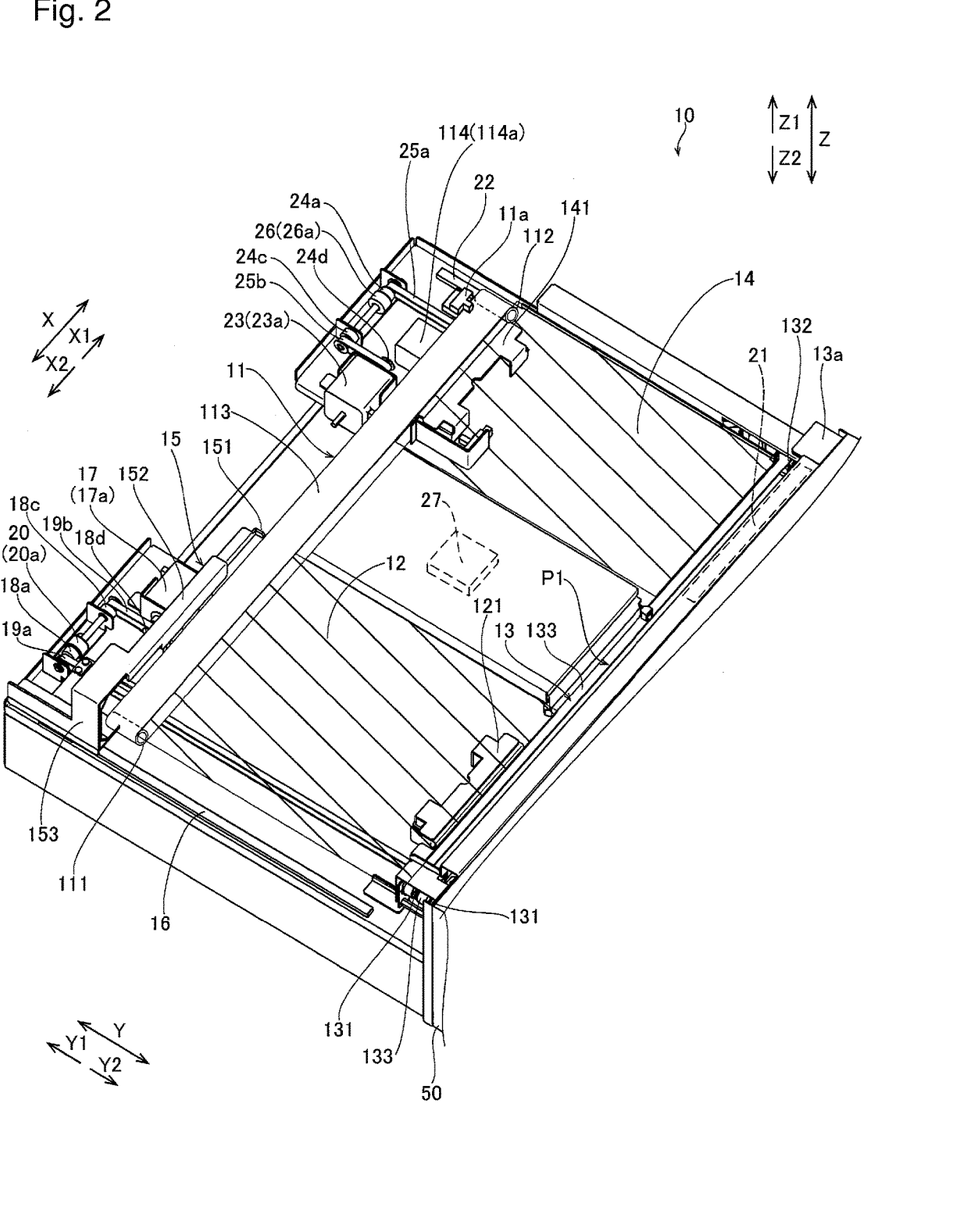
FIG. 2 is a perspective view illustrating the transport apparatus according to an embodiment.

As illustrated in FIG. 2, as the mechanism to drive first movable member 15, transport apparatus 10 includes guide member 16, drive unit 17, pulleys 18a to 18d (see FIG. 3), belts 19a and 19b, and transmission blocking mechanism 20. As the mechanism to drive second movable member 21, transport apparatus 10 includes guide member 22, drive unit 23, pulleys 24a to 24d (see FIG. 3), belts 25a and 25b, and transmission blocking mechanism 26. Note that, in FIG. 2, rack sender unit 12 and rack delivery unit 14 are illustrated with diagonal lines for the sake of convenience of the description.

As illustrated in FIG. 2, using support part 153 at its X2-side end as a base end, first movable member 15 supports second portion 152 extending in the X1 direction and first portion 151 provided in its end portion in the X1 direction. Support part 153 is fixed on belt 19*a*. In other words, second portion 152 is supported by support part 153 at its X2-side end only. Support part 153 slidably engages with guide member 16.

Guide member 16 is a rail member that slidably engages with support part 153. Guide member 16 extends linearly along the Y axis. Guide member 16 guides the movement of first movable member 15 between first position L1 (see FIG. 1) and second position L3 (see FIG. 1).

Drive unit 17 includes pulse motor 17*a*, for example. Drive unit 17 is a drive source to move first movable member 15. Pulse motor 17*a* performs drive control based on the number of pulses. Note that a servo motor other than pulse motor 17*a* may be used for drive unit 17.

Figure 3:
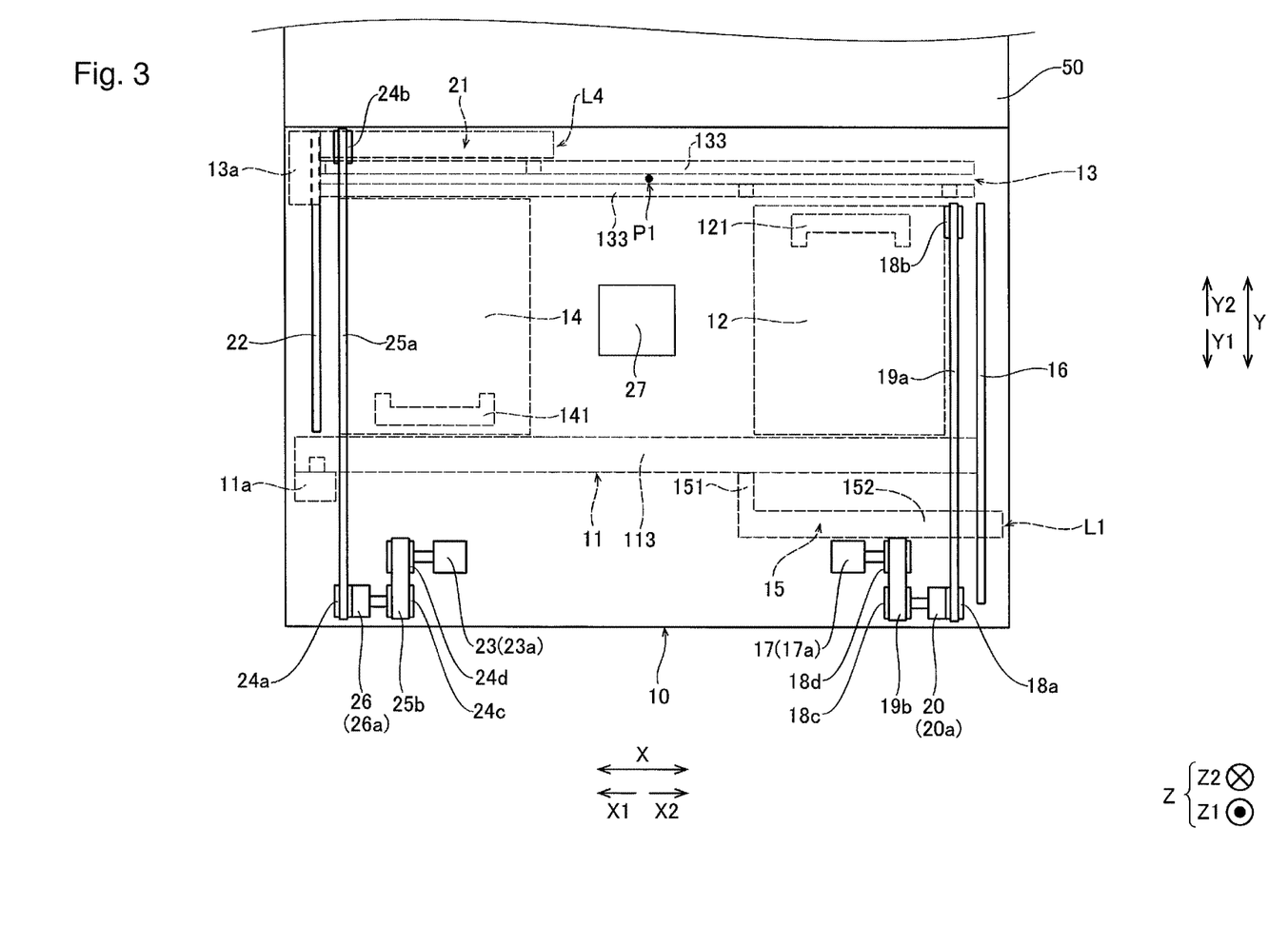
FIG. 3 is a diagram illustrating a drive unit in the transport apparatus according to an embodiment, the drive unit drives each of a first movable member and a second movable member.

As illustrated in FIG. 3, the shaft of drive unit 17 is connected to pulley 18*d*. Circular belt 19*b* is wound around pulley 18*d* and pulley 18*c*. Pulley 18*c* has a shaft connected to pulley 18*a* via transmission blocking mechanism 20. Circular belt 19*a* is wound around pulley 18*a* and pulley 18*b*. Support part 153 of first movable member 15 described above is fixed on belt 19*a* while slidably engaging with guide member 16. When drive unit 17 drives pulse motor 17*a*, the driving force is transmitted to pulleys 18*a* to 18*d* and moves belt 19*a*. First movable member 15 is moved in conjunction with the movement of belt 19*a*.

Transmission blocking mechanism 20 includes torque limiter 20*a*. Transmission blocking mechanism 20 blocks transmission of the driving force to first movable member 15 by drive unit 17 when receiving a load of a certain level or more. More specifically, when transmission blocking mechanism 20 receives the load of the certain level or more, the shaft which connects pulleys 18*c* and 18*a* runs idle by the action of torque limiter 20*a* and the transmission of the driving force is blocked, which stops the movement of first movable member 15.

As first movable member 15 is moved in the Y2 direction under control of controller 27, rack 900 is moved in the Y2 direction along with the movement of first movable member 15. At this time, there is a difference in the arrival position of rack 900 between the cases where restriction unit 121 projects above rack sender unit 12 and where restriction unit 121 does not project above rack sender unit 12.

In the case where restriction unit 121 projects above rack sender unit 12, rack 900 pushed by first movable member 15 comes into contact with restriction unit 121. When rack 900 comes into contact with restriction unit 121, transmission blocking mechanism 20 receives the load of the certain level or more and thus blocks transmission of the driving force. This makes drive unit 17 run idle and a remaining amount of the driving force run out. Rack 900 is stopped while abutting on restriction unit 121. If other racks 900 already exist in rack sender unit 12, all racks 900 in rack sender unit 12 are pushed rearward (in the Y2 direction) by first movable member 15. In this case, the load applied to transmission blocking mechanism 20 becomes the certain level or more when first rack 900 comes into contact with restriction unit 121, which actuates transmission blocking mechanism 20 and stops first movable member 15.

In the case where restriction unit 121 does not project above rack sender unit 12, rack 900 pushed by first movable member 15 passes through rack sender unit 12 and is sent to second transport unit 13. If other racks 900 already exist in rack sender unit 12, all racks 900 in rack sender unit 12 are pushed rearward (in the Y2 direction) by first movable member 15. In this case, the load applied to transmission blocking mechanism 20 becomes the certain level or more when first rack 900 is sent to second transport unit 13, which actuates transmission blocking mechanism 20 and stops first movable member 15.

With this configuration, rack 900 pushed by first movable member 15 is stopped at the position where rack 900 cannot move any more in the Y2 direction, and the transmission of the driving force of drive unit 17 is blocked. Thus, it is unnecessary to change the amount of the driving force of drive unit 17 depending on a distance by which rack 900 needs to move. Besides, this configuration makes it possible to prevent drive unit 17 from generating abnormal chattering noise due to application of a load.

When the amount of the driving force runs out, controller 27 returns first movable member 15 back to position of origin L1.

The number of pulses generated by drive unit 17 when first movable member 15 returns to position of origin L1 corresponds to a position on the Y axis of rack 900 which is located at a foremost position (in the Y1 direction) among racks 900 in rack sender unit 12. This corresponds to the number of racks 900 in rack sender unit 12. Accordingly, controller 27 calculates the number of racks 900 in rack sender unit 12 based on the number of pulses generated by drive unit 17 (see FIG. 3) when first movable member 15 returns to position of origin L1. Based on the calculation result, controller 27 can judge whether or not the maximum number of racks 900 that can remain in rack sender unit 12 is equal to the number of racks 900 currently remaining in rack sender unit 12 (packed state). If judging that rack sender unit 12 is in the packed state, controller 27 no longer sends rack 900 to rack sender unit 12.

Guide member 22, drive unit 23, pulleys 24*a* to 24*d*, belts 25*a* and 25*b*, and transmission blocking mechanism 26, which constitute the mechanism to drive second movable member 21, respectively correspond to guide member 16, drive unit 17, pulleys 18*a* to 18*d*, belts 19*a* and 19*b*, and transmission blocking mechanism 20, which constitute the mechanism to drive first movable member 15. Second movable member 21 can move along the Y axis similarly to first movable member 15. Second movable member 21 moves along the Y axis to move rack 900 on second transport unit 13 to rack delivery unit 14. As in the case of first movable member 15, controller 27 is capable of judging whether or not rack delivery unit 14 is in the packed state based on the number of racks 900 in rack delivery unit 14 calculated based on the number of pulses generated by drive unit 23 when second movable member 21 returns to third position L4.

Returning to FIG. 2, first transport unit 11 includes first pulley 111, second pulley 112, and drive unit 114.

First pulley 111 is arranged on the upstream side in the transport direction (on the X2 side). Second pulley 112 is arranged on the downstream side in the transport direction (on the X1 side). Circular transport belt 113 is wound around first pulley 111 and second pulley 112. Transport belt 113 is driven via first and second pulleys 111 and 112 upon transmission of the driving force of drive unit 114.

Support part 153 is movable along the Y axis while passing through the outside (X2 side) of first pulley 111 and second pulley 112 of first transport unit 11. Specifically, support part 153 is located at the X2 side than first pulley 111 of first transport unit 11. Thereby, support part 153 does not need to traverse transport belt 113 and thus division of transport belt 113 is not needed, which simplifies the structure of transport apparatus 10.

Similarly to first transport unit 11, second transport unit 13 includes two first pulleys 131, two second pulleys 132, and two drive units (not shown). Two transport belts 133 are driven individually via first pulleys 131 and second pulleys 132 upon transmission of the driving force of the drive units (not shown). Note that, in FIG. 2, one of two second pulleys 132 is not illustrated.

Next, a system including transport apparatus 10 is described with reference to FIG. 4.

Figure 4:
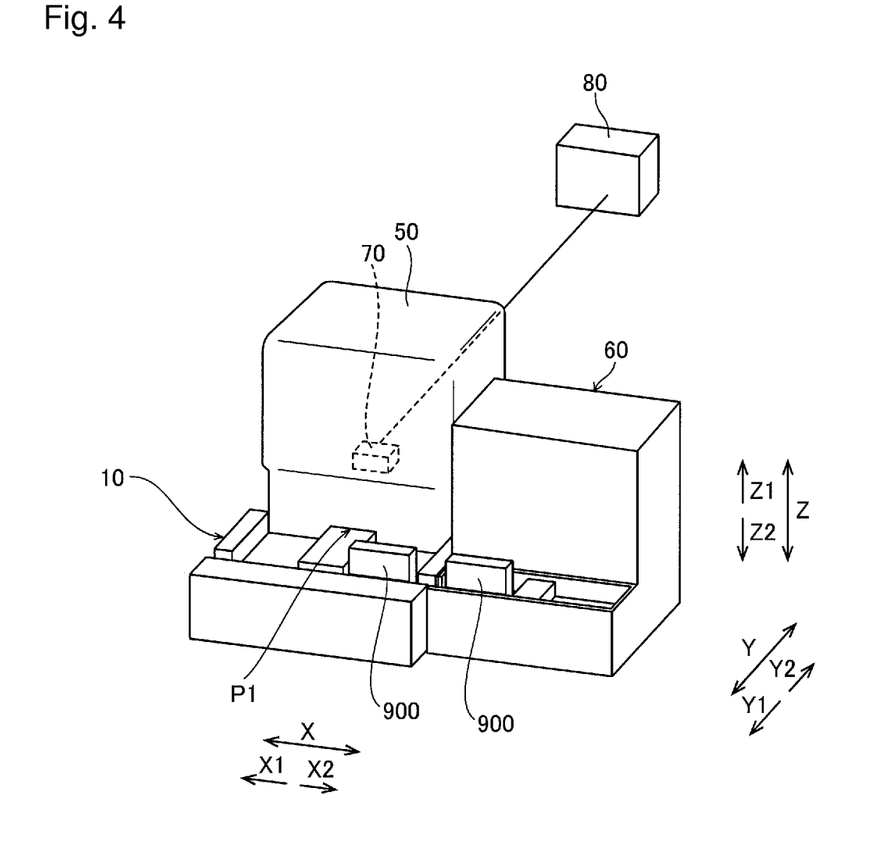
FIG. 4 is a view of a transport apparatus connected to another device.

As illustrated in FIG. 4, transport apparatus 10 is connected to sample input device 60. Measurement device 50 is connected to information processing unit (IPU) 70 constituted by a computer. Transport apparatus 10 is connected to host computer 80 via IPU 70 of measurement device 50.

Measurement device 50 is arranged at the Y2 side of transport apparatus 10. Measurement device 50 sucks a urine sample transported to sample loading position P1 by transport apparatus 10 and tests the urine. IPU 70 analyzes measurement data that measurement device 50 has acquired through the urine sample measurement and thereby generates a test result.

In sample input device 60, racks 900 housing samples therein are set by the user. Sample input device 60 transports rack 900 to transport apparatus 10 in response to a request by transport apparatus 10.

Host computer 80 comprises a PC. Host computer 80 stores therein a measurement order of urine samples, and sends the measurement order in response to a request by measurement device 50. Host computer 80 also receives and stores a test result obtained by measurement device 50 according to the measurement order.

According to the embodiment, first movable member 15 can move rack 900 directly from first transport unit 11 to second transport unit 13. Thus, the structure of transport apparatus 10 can be simplified unlike the case where first movable member 15 passes rack 900 in first transport unit 11 to another member and then this member moves rack 900 to second transport unit 13.

In Patent Literature 1, a rack is moved from the first transport unit to the second transport unit by being passed from the movable member to the rack transfer member, which complicates the structure of the transport apparatus. Hence, there is a demand for simplification of the structure of the transport apparatus.

Embodiments described above simplify the structure of a transport apparatus.

Note that embodiments disclosed herein should be deemed exemplary and not restrictive in every respect. The scope of embodiments is not defined by the description of the embodiment described above but by the scope of the claims, and includes changes having the same meaning and scope within the scope of the claims.

The invention claimed is:

1. A transport apparatus that transports a rack that holds a sample container, the transport apparatus comprising:
   a first transport unit comprising a first transport belt configured to transport the rack on a first path between two ends of the transport apparatus;
   a second transport unit comprising a second transport belt configured to transport the rack on a second path that extends parallel to the first path of the first transport unit;
   a rack sender unit interposed between the first transport unit and the second transport unit and comprising an upper surface configured to support a plurality of racks, the upper surface extending in a first direction that intersects a second direction in which the first path and the second path extend;
   a first movable member comprising a first portion extending in the first direction and a second portion extending in the second direction, the first portion being formed at a side end of the second portion in the second direction;
   a drive unit configured to move the first movable member between the first transport unit and the second transport unit;
   a torque limiter that blocks transmission of a driving force applied to the first movable member by the drive unit, when the torque limiter responds to a threshold load; and
   a projection capable of a positional change between a contact mode in which the projection contacts a rack moving in the rack sender unit, and a non-contact mode in which the projection is kept from contact with the rack, and the projection restricts a movement of the rack from the rack sender unit to the second transport unit thereby keeping the rack in the rack sender unit when the projection is in the contact mode, wherein
   in the contact mode, the projection is configured to restrict movement of the rack and the drive unit moves the first movable member toward the second transport unit until the torque limiter blocks the transmission of the driving force due to application of the threshold load by the projection,
   the first portion of the first movable member contacts, at a position above the first path, the rack transported by the first transport unit to stop the rack at a rack stop position on the first path,
   the second portion of the first movable member pushes, in the first direction, a side surface of the rack located at the rack stop position on the first path, and transports the rack from the rack stop position in the first direction and stops the transported rack at the second path beyond the upper surface, and
   the second transport unit moves the rack transported by the first movable member to a sample loading position, the sample loading position located on the second path between the rack sender unit on the one of the two ends of the transport apparatus and a rack delivery unit on the other of the two ends of the transport apparatus.

2. The transport apparatus according to claim 1, wherein the first movable member is movable in the first direction between a first position and a second position, wherein
   in the first position, the first movable member is moved in the first direction away from the first path such that the first portion does not interfere with the rack in a condition in which the rack is transported by the first transport unit on the first path, and
   in the second position the second portion pushes, in the first direction, the side surface of the rack, so as to place the rack onto the second path of the second transport unit.

3. The transport apparatus according to claim 2, further comprising:
   a guide member that guides movement of the first movable member between the first position and the second position.

4. The transport apparatus according to claim 3, wherein the rack comprises a plurality of racks, the drive unit comprises a pulse motor, and
the transport apparatus further comprises a controller that counts a number of the plurality of racks remaining in the rack sender unit based on a number of pulses of the pulse motor generated during a return of the first movable member back to the first position after the first movable member is moved to the second position.

5. The transport apparatus according to claim 1, wherein only an end of the first movable member on an upstream side of the first transport unit is supported by a support part.

6. The transport apparatus according to claim 5, wherein
the first path of the first transport unit comprises a transport direction,
the second portion extends in a longitudinal direction of the rack,
only an end of the second portion on the upstream side of the transport direction of the first transport unit is supported by the support part, and
the first portion is provided at an opposite end of the first movable member from the end of the second portion on the upstream side of the transport direction of the first transport unit.

7. The transport apparatus according to claim 6, wherein the first transport unit comprises
a first pulley located on the upstream side thereof in the transport direction,
a second pulley located on a downstream side thereof in the transport direction, and
the first transport belt wound around the first pulley and the second pulley, and wherein
the support part is movable in the first direction while passing outside of an area defined by the first pulley, the second pulley and the first transport belt, the support part located closer to the first pulley on the upstream side of the first transport unit than the second pulley.

8. The transport apparatus according to claim 1, wherein
the rack delivery unit extends between the first transport unit and the second transport unit in the first direction intersecting the first path of the first transport unit on the other of the two ends of the transport apparatus, and receives the rack in a condition in which the second transport unit moves the rack holding the sample container on the second path of the second transport unit through the sample loading position to a rack stop position on the second path of the second transport unit,
the transport apparatus further comprises a second movable member that moves the rack in the first direction, and
the second movable member is capable of moving the rack located at the rack stop position on the second path of the second transport unit to an end of the rack delivery unit adjacent to the first transport unit.

9. The transport apparatus according to claim 8, wherein the rack delivery unit comprises a projection which is capable of positional change between a contact mode where the projection contacts the rack moving in the rack delivery unit, and a non-contact mode where the projection is kept from contact with the rack,
wherein the projection restricts a movement of the rack from the rack delivery unit to the first transport unit when the projection is in the contact mode.

10. The transport apparatus according to claim 9, wherein the projection of the rack delivery unit is in the contact mode.

11. The transport apparatus according to claim 1, wherein the drive unit is configured to provide a constant driving force.

* * * * *